United States Patent [19]

Nakanishi et al.

[11] Patent Number: 5,395,359
[45] Date of Patent: Mar. 7, 1995

[54] ABSORBENT ARTICLE

[75] Inventors: Minoru Nakanishi, Minamikawachi; Satoshi Yamamoto; Mitsugu Hamajima, both of Utsunomiya; Yukimitsu Koseki, Mashiko, all of Japan

[73] Assignee: Kao Corporation, Tokyo, Japan

[21] Appl. No.: 127,122

[22] Filed: Sep. 27, 1993

Related U.S. Application Data

[63] Continuation of Ser. No. 825,103, Jan. 24, 1992, abandoned.

[30] Foreign Application Priority Data

Jan. 25, 1991 [JP] Japan .................. 3-025714

[51] Int. Cl.$^6$ ............................... A61F 13/15
[52] U.S. Cl. ..................................... 604/378
[58] Field of Search .............. 604/368, 369, 378, 379, 604/385.1

[56] References Cited

U.S. PATENT DOCUMENTS

| | | | |
|---|---|---|---|
| 3,356,090 | 12/1967 | Plantinga et al. | 604/368 |
| 3,528,421 | 9/1970 | Vaillancourt et al. | 604/368 |
| 3,888,256 | 6/1975 | Studinger | 604/368 |
| 3,903,889 | 9/1975 | Torr | 604/368 |
| 4,269,188 | 5/1981 | Nishizawa et al. | 604/368 |
| 4,287,251 | 9/1981 | King et al. | 604/368 |
| 4,381,784 | 5/1983 | Aberson et al. | 604/368 |
| 4,589,877 | 5/1986 | Sivilich | 604/385.1 |
| 4,600,458 | 7/1986 | Kramer et al. | 604/368 |
| 4,798,601 | 1/1989 | Shirose et al. | 604/378 |
| 4,850,991 | 7/1989 | Nakanishi et al. | 604/369 |
| 4,851,284 | 7/1989 | Yamanoi et al. | 428/284 |
| 4,857,065 | 8/1989 | Seal | 428/284 |
| 5,004,465 | 4/1991 | Ternström et al. | 604/385.1 |
| 5,037,418 | 8/1991 | Kons et al. | 604/387 |
| 5,072,687 | 12/1991 | Mitchell et al. | 118/37 |
| 5,091,240 | 2/1992 | Kajander et al. | 604/365 |

FOREIGN PATENT DOCUMENTS

| | | |
|---|---|---|
| 0033235 | 1/1981 | European Pat. Off. . |
| 54-141099 | 1/1979 | Japan . |
| 54-123293 | 9/1979 | Japan . |
| 54-158096 | 12/1979 | Japan . |
| 55-14024 | 1/1980 | Japan . |
| 59-26467 | 6/1984 | Japan . |
| 60-63043 | 4/1985 | Japan . |
| 60-185551 | 9/1985 | Japan . |
| 2004201 | 8/1978 | United Kingdom . |
| 2132897 | 7/1984 | United Kingdom . |
| 8605089 | 9/1986 | WIPO . |

*Primary Examiner*—Randall L. Green
*Assistant Examiner*—Rob Clarke
*Attorney, Agent, or Firm*—Birch, Stewart, Kolasch & Birch

[57] ABSTRACT

An absorbent article which comprises an absorbent element which at least partially comprises an absorbent sheet A prepared by applying a pressure-sensitive adhesive 3 having a suitable adhesive power to an absorbent material 1 having a suitable liquid-absorbent (or retentive) power in the form of dot, line or curve (spiral curve or the like) with the pressure-sensitive adhesive in a suitable density; spreading an absorbent polymer 2 thereon; putting another sheet of the absorbent material 1 thereon, and compressing the assemblage into a composite structure. In the course of the absorption of a liquid, the liquid is first stocked in the absorbent material having a high initial absorption velocity, and is gradually transferred to the absorbent polymer by capillary power as the driving force and absorbed therein, while the absorbent polymer is prevented from falling off from the absorbent material by the pressure-sensitive adhesive, whereby the properties of the absorbent polymer can be exhibited to the fullest.

14 Claims, 1 Drawing Sheet

ABSORBENT ARTICLE

This application is a continuation of application Ser. No. 07/825,103 filed on Jan. 24, 1992, now abandoned.

BACKGROUND OF THE INVENTION

1. Field of the Invention

The present invention relates to absorbent articles for body fluid, such as sanitary napkins, paper diapers, surgical pads and breast milk sheets. In particular, the present invention relates to an absorbent article comprising an absorbent element which partially or wholly comprises an absorbent sheet made from an absorbent material having liquid absorbent (or retentive) power and an absorbent polymer weakly fixed on the absorbent material with a pressure-sensitive adhesive applied thereto in the form of a dot, a line or a curve.

1. Description of the Prior Art

The absorbent element of conventional absorbent articles such as sanitary napkins or paper diapers mainly comprises a fluffy pulp, an absorbent paper and an absorbent polymer. Among them, a highly absorbent polymer is present in most of the absorbent articles at present, since it has a high absorption capacity and solidifies the fluid into a gel so that the fluid cannot leak out once absorbed.

In spite of having such excellent characteristics, however, the absorbent polymer has a technical problem in that it tends to fall off i.e., it easily leaks out of the absorbent article, since it is powdery. In addition, there is a demand to further improve the essential absorption capacity of the absorbent polymer. Since the falling off of the absorbent polymer is a fatal defect for the absorbency properties of the absorbent article, various processes for preventing the falling off (i.e. for the fixation) of the absorbent polymer have heretofore been proposed.

The prior-art processes heretofore proposed for preventing the falling off i.e. for the fixation of the absorbent polymer comprises bonding the absorbent polymer to a base to be combined therewith by a means such as:

(1) the bonding of the absorbent polymer to the base with water, (2) the application of an adhesive to the base followed by the adhesion of the absorbent polymer thereto to form a sandwich structure, or (3) the bonding of the absorbent polymer by means of a heat-fusible fiber (non-woven fabric) or film.

The first bonding means (1) was proposed, for examples, in Japanese Patent Publication No. 2647/1984 and Japanese Patent Laid-Open Nos. 123293/1979 and 141099/1979. However, these processes wherein the absorbent polymer is swollen with water and fixed have problems in that when the absorbent polymer is impregnated with water in a quantity sufficient for fixation to soften the gel before fixation, the absorbent polymer is crushed in the fixing step to impair the essential absorbent properties of the absorbent polymer and, in addition, the water cannot be evenly spread in the entire absorbent polymer layer and the part of the absorbent polymer layer in which the gel adhesion is insufficient, falls off.

The second bonding means (2) was proposed, for example, in Japanese Patent Laid-Open No. 63043/1985. In this process wherein the absorbent polymer is bonded to the base by means of an adhesive, the absorbent polymer can be prevented from falling off to a considerable extent. However, it also has the defects that since the hydrophilic properties of the adhesive are insufficient, the absorbency of the base is seriously reduced and, as a result, the properties of the absorbent polymer cannot be sufficiently exhibited and that since the absorbent polymer is completely fixed to the base, it cannot be released from fixation and, therefore, the swelling of the absorbent polymer is inhibited, thereby seriously lowering the absorption rate.

The third bonding means (3) was proposed, for example, in Japanese Patent Laid-Open Nos. 158096/1979 and 14024/1980. However, these processes also have the problem of impairing the properties of the absorbent polymer as described in the above item (2).

Thus it has been demanded in the prior art to develop a process which satisfies the two requirements, i.e. the prevention of the falling off of the absorbent polymer without sacrificing the absorbing properties of the absorbent polymer per se.

SUMMARY OF THE INVENTION

An object of the present invention is to provide an absorbent article having improved absorbent properties and is prevented from falling off of the absorbent polymer.

This object can be attained by providing an absorbent sheet used for part or all of the absorbent element in an absorbent article comprising a liquid-permeable layer, a liquid-retentive absorbent element and a liquid-impermeable anti-leakage material, said absorbent sheet being disposed with an absorbent polymer fixed on an absorbent material by a hot melt adhesive applied thereto in the form of a dot, a line or a curve.

The absorbent article of the present invention exhibits improved absorption properties and prevents the absorbent polymer from falling off.

BRIEF DESCRIPTION OF THE DRAWINGS

The present invention will become fully understood from the detailed description given hereinbelow and the accompanying drawings which are given by way of illustration only, and thus, are not limitative of the present invention, and wherein.

DETAILED DESCRIPTION OF THE INVENTION

Figure 1:
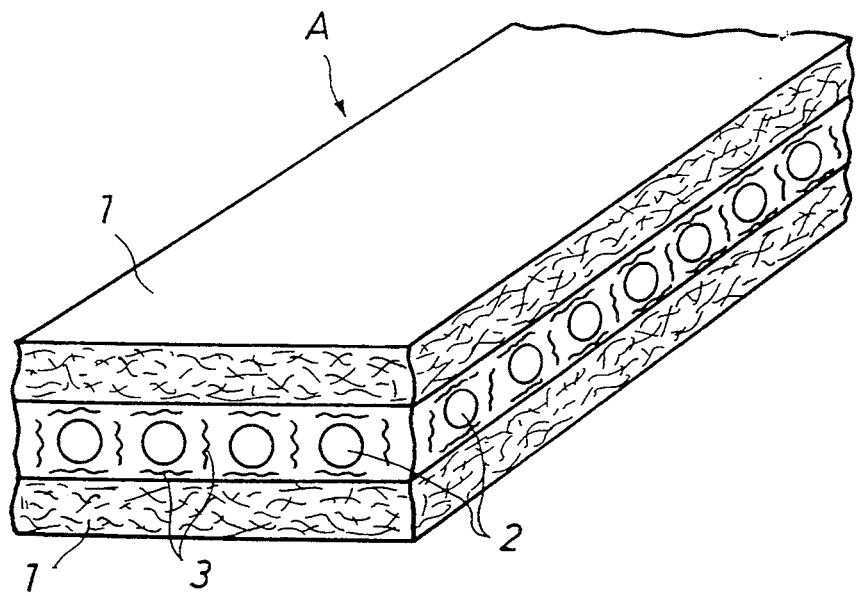
FIG. 1 is a perspective view showing elements of the absorbent sheet of the present invention.

As shown in the FIG. 1, an absorbent sheet A, a preferable example of the present invention, is prepared by applying a pressure-sensitive adhesive 3 having suitable adhesive power in the form of a dot, a line or a curve (such as a spiral) at a suitable density on an absorbent material 1 having suitable liquid-absorbent (or retentive) power, then spreading an absorbent polymer 2 thereon, placing another absorbent material 1 thereon, and compressing the components together to form a one piece composite structure.

The compression into a one piece composite structure can be combined with various after-processing steps such as embossing to control the diffusion direction, diffusion velocity, etc. into the absorbent sheet.

The absorbent material having a suitable liquid-absorbent (or retentive) power plays an important role for causing the absorbent polymer to exhibit its full effect.

The absorbent material has the following properties:
(1) it improves the efficiency of contact of the absorbent polymer with the liquid to a maximum extent (the absorbent polymer is sufficiently wetted with the liquid);
(2) the absorbent polymer acts as a temporary stock layer before it has completely absorbed the liquid; and
(3) the difference in the liquid absorbency between the absorbent polymer and the absorbent material is sufficient so that the liquid, once absorbed in the absorbent material, will smoothly migrate to the absorbent polymer (i.e. liquid-absorbent power or the absorbent polymer > liquid-absorbent power of the absorbent material).

These properties vary depending on the average capillary diameter and wettability of the absorbent material (fiber aggregate) and it is important to optimize the properties.

The inventors noted the Klemm absorption (JIS P 8141) from which factors relating to both average capillary diameter and wettability can be evaluated by using two or more test liquids (such as water and ethanol) and have succeeded in defining the preferable ranges of the properties of the absorbent material satisfying the above requirements (1) to (3).

The following definition is described in JIS P 8141.

JAPANESE INDUSTRIAL STANDARD

Testing Method for Water Absorption of Paper by Klemm's Method

1. Scope

This Japanese Industrial Standard specifies the testing method for water absorption of paper large in water absorbing property by water absorption height.

2. Apparatus
   (1) Second watch
   (2) Lengthmeter: the lengthmeter having mm scale
   (3) Container to put in water
   (4) Supporting fitting: the fitting to suspend the test piece and lengthmeter.

3. Test Piece

Take the paper for test according to JIS P 8110, and allow to comply with the conditions of JIS P 8111. Make the test piece 15 mm in width, 120 mm or more in length, and take correctly, respectively five or more sheets in longitudinal and lateral directions. Take the piece of which long side is parallel to longitudinal direction as the longitudinal direction test piece and that is parallel to the lateral direction, as the lateral direction test piece.

4. Operation

The test shall be carried out in the atmosphere complying with the conditions of JIS P 8111. For water to be put into the container, distilled water shall be used and its temperature, be 15° to 20° C.

As to test piece, draw a marked line at a place of 5 mm from the short side in parallel to it by using a pencil, keep vertically, put into water quickly until the marked line and read out the height until the position of center of paper width where the water risen in 1 min or in 10 min by unit of mm. Hold the length meter in parallel to the test piece and it is not allowed to contact with the test piece during measuring.

5. Report

The water absorption height risen of test piece in 1 min or 10 min shall be expressed by mm to be taken as the water absorption. Relating to respective directions, the average value, water absorption time shall be reported, and if required, the maximum value, minimum value and number of measuring, appended.

To satisfy the above-described requirements, the Klemm's water absorption of the absorbent material after 1 min must be 20 mm to 150 mm (water absorption height when ion-exchanged water is used as the test liquid). When this height is lower than 20 mm, the absorbent polymer is not sufficiently wetted with the liquid to cause an insufficient absorption and, in addition, since the liquid-absorbent power of the absorbent material is insufficient, a problem is caused wherein the liquid once absorbed is released outside before the absorbent polymer has completely absorbed it.

On the contrary, when the Klemm absorption is too high, the liquid-absorbing power of the absorbent material becomes too high and the liquid cannot smoothly migrate into the absorbent polymer layer. As the result, the absorption rate of the absorbent polymer is seriously reduced.

The average capillary size of the absorbent material is preferably 300 $\mu$m or less, advantageously 0.5 $\mu$m to 300 $\mu$m, so that the absorbent polymer is firmly fixed on the absorbent material (base).

Various absorbent materials are usable so far as they have the above-described in dispensable properties. They include nonwoven fabrics (dry/wet) of synthetic fibers suitably treated to impart hydrophilic properties thereto, nonwoven fabrics of hydrophilic fibers such as pulp, rayon, cotton or hemp and sheets such as paper. As a matter of course, the wetting properties and average capillary diameter must be carefully designed.

Examples of the synthetic fibers include polyolefin fiber such as polyethylene fiber and polypropylene fiber, polyester fiber, polyethylene-polypropylene composite fiber, polyethylene-polyester composite fiber, low-melting polyethylene composite fiber, polyvinylalcohol fiber, polyvinylalcohol-polypropylene composite fiber and polyvinylalcohol-polyester composite fiber.

A description will now be made of the preferred properties of the absorbent polymer to be fixed on to the absorbent material with the adhesive.

For preventing the absorbent polymer from undergoing the inhibition of swelling when it is swollen with a liquid, it is necessary that the absorbent polymer fixed on the absorbent material be released by the swelling pressure of the polymer during the absorption of the liquid. To exhibit a high swelling pressure, the absorbent polymer must have a high expansion rate.

For this purpose, the absorption of the absorbent polymer must be at least 30 g/g, when physiological saline is used as the test liquid. Further, to smoothly withdraw the liquid from the absorbent material, the absorbent polymer must exhibit a high liquid absorbing velocity.(sucking power). Namely, it must have an absorbing capacity of at least 8.0 ml/0.3 g in 20min, when physiological saline is used as the liquid, advantageously 8.0 ml/0.3 g to 20 ml/0.3 g in 20 min. Examples of the preferable absorbent polymer having such properties and usable herein are those described in Japanese Patent Laid-Open No. 185551/1985, more preferably, acrylic acid (salt) crosslinked polymer in which the bridge structure is specifically controlled.

The amount of the absorbent polymer to be spread is preferably 150 g/m$^2$ or less, advantageously 10 g/m$^2$ to 150 g/m². When it is less than 10/m² a suffcient absorption effect cannot be obtained. When it exceeds 150 g/m², the absorbent polymer layer becomes too thick and the absorption is inhibited by gel blocking during the swelling of this polymer or a part of the polymer does not become completely fixed causing the adhesive to leak out.

A description will now be made of the adhesive for fixing the absorbent polymer onto the absorbent material.

The pressure-sensitive adhesive used in the present invention has suitable adhesive properties so as to prevent scattering or falling of the absorbent polymer during the preparation of the sheet and to keep the absorbent polymer fixed on the absorbent material. It is also necessary that the adhesive does not inhibit the absorption and diffusion of the liquid so as to make the sufficient wetting of the absorbent polymer with the liquid possible during the absorption of the liquid and to facilitate the release of the absorbent polymer from fixation so that the swelling of the polymer is not inhibited during the swelling of the polymer.

To exhibit this function, the absorbent polymer fixed on the absorbent material with the adhesive must be released by the swelling pressure of the polymer and the design of a suitable peel adhesion is important. To obtain the intended properties, the 180° peel adhesion of the adhesive (JIS C 2107) is preferably 4000 g or less, advantageously 500 g to 4000 g. Further to fix the absorbent polymer without impairing the wettability and diffusing properties of the absorbent material, the adhesive must be spread not on the entire surface of the absorbent material but on parts thereof in the form of a dot, a line or a curve. To exhibit the properties of the absorbent polymer to the fullest without causing the falling off of the absorbent polymer, it is important that the adhesive be applied in a suitable density within such a range that the area occupied by the adhesive will not exceed 70%, advantageously 10% to 70%.

Particular examples of the pressure-sensitive adhesives having the properties in the ranges described above and usable herein include various adhesives such as acrylic ester copolymers, vinyl acetate / acrylic ester copolymers, ethylene / olefin copolymers, ethylene / butadiene copolymer and petroleum adhesive resins. A hot melt adhesive is preferable. Examples of the hot melt adhesive include P-618B (trade name) of Toyo-Petrolite Co., Ltd., MQ-916 (trade name) of Kanebo-NSC Ltd. and HT 400 ZB (trade name) of Nitta Gelatin Inc. Any pressure-sensitive adhesive having the above-described properties can be used without any limitation.

In the absorbent article of the present invention, a part or the whole of the absorbent element comprises the above-described absorbent sheet.

When the absorbent sheet comprising the absorbent material, absorbent polymer and the pressure-sensitive adhesive each having the properties described above is used as the absorbent element, the absorbent article of the present invention exhibits an excellent effect.

The absorbent polymer can be fully swollen in such an environment that the liquid to be absorbed thoroughly wets the surrounding polymer whereby the resistance to the migration of the liquid to the absorbent polymer is very low. In practice the liquid migrates in the absorbent article such that the liquid is first stocked in the absorbent material having a high initial absorption velocity, then gradually spreads to wet the surrounding absorbent polymer, and then is driven to the absorbent polymer by a driving force (i.e. the difference $\Delta P$ between the capillary power of the absorbent material and the osmotic pressure of the absorbent polymer), and absorbed therein.

Therefore, although the liquid-diffusing power sufficient for thoroughly wetting the absorbent polymer is required of the absorbent material, the capillary power of the structure (absorbent material) is desirably as low as possible. Thus for exhibiting the maximum effect of the absorbent polymer, the balance of the osmotic pressure (capillary power) between the absorbent polymer and the absorbent material is quite important for the above-described reasons.

Both the absorbent polymer and the absorbent material have their own properties suitable for exhibiting the maximum effects thereof. The present invention has succeeded in defining the suitable physical properties of these elements. Namely, for sufficiently diffusing the liquid, the quantity of diffusion per unit time in the initial stage of the absorption is at least 20 mm (after one minute) (in terms of the Klemm absorption employed for indirectly indicating the quantity of dispersion).

However, when such conditions are to be satisfied by the absorbent material, the absorbing capacity of the absorbent polymer to be combined with the absorbent material is seriously reduced, since the difference between the osmotic pressure of the absorbent polymer and the capillary power of the capillary structure (absorbent material) is only small as compared with that in the case of free swelling (swelling in a large excess of the liquid). Therefore, the absorbent polymer must have a high osmotic pressure sufficient for overcoming this defect. Under these conditions, the object of the present invention cannot be attained unless the absorbent power (osmotic pressure) of the absorbent polymer is above a certain level. It has been found that the necessitated properties of the absorbent polymer (in an indirect expression in terms of the liquid absorption velocity, i.e. the velocity of absorption of the liquid by the absorbent polymer from the structure are at least 8.0 ml/0.3 g (after 20 min). However, even when the liquid-absorbing capacity (osmotic pressure) of the absorbent polymer is designed to be high, the effect is seriously impaired when the capillary power of the absorbent material is too high.

The pressure-sensitive adhesive can be applied by any ordinary application method such as spray coating. The application method is not particularly limited so far as the above-described occupied area rate can be secured.

The quantity of the pressure-sensitive adhesive to be applied varies depending on the method of application. For example, when a hot melt adhesive P-618 B (Toyo-Petrolite Co., Ltd.) is applied in a spiral form by spray coating, the optimum quantity is 1 to 50 g/m².

Further description will be made referring to the adhesion condition when the adhesive is applied in the form of a dot, a line or a curve. The area occupied by the adhesive is preferably from 10% to 70%, as mentioned above. Furthermore, it is not desirable that the part to which the adhesive is applied exists in the wide range continuously. It is desirable that the part to which the adhesive is not applied certainly exists in a circle of 10 to 30 mm in diameter.

Therefore, when the adhesive is applied in the form of a dot, the size of the dot is preferably 0.1 to 10 mm in diameter. Further when the adhesive is applied in the form of a line or a curve, the width of the line is preferably 0.05 to 5 mm, and the width of the part to which the adhesive is not applied between the lines is preferably 0.05 to 10 mm.

Although the absorbent sheet thus obtained can be used as it is as the absorbent element, its function is further improved by combining it with another absorbent material such as a fluffy pulp or absorbent paper depending on the use and the combination which can be used as various absorbent articles.

A detailed description will now be made as to the synergism of the properties of the three components, i.e. the absorbent material, absorbent polymer and pressure-sensitive adhesive, which are the essential constituents of the present invention.

The capillary power of the absorbent material must not exceed $1.5 \times 10^4$ dyn/cm$^2$ advantageously $0.2 \times 10^4$ to $1.5 \times 10^4$ dyn/cm$^2$ or, in terms of the Klemm absorption, it must not exceed 150 nun/min.

The relationship between the properties of the absorbent material and those of the absorbent polymer has been thus made apparent. For attaining the second object of the present invention, i.e. the complete inhibition of the falling off of the absorbent polymer without inhibiting the swelling of the absorbent polymer, the balance of the properties of the materials which will be described below are further necessitated.

Although a suitable adhesive power is necessitated for the pressure-sensitive adhesive for fixing the absorbent polymer before the absorption of the liquid, it is important that the adhesive power be easily released by a high swelling pressure generated when the absorbent polymer absorbs the liquid in the step of swelling the absorbent polymer. For this purpose, the rate of swelling of the absorbent polymer by the absorption of the liquid must be designed to be high. By the swelling (expansion) pressure and the large volume after the swelling, the polymer is released from the bonding caused by the adhesive and free swelling thereof is made possible.

After intensive investigations, it has been found that for releasing the absorbent polymer, which is temporarily fixed with the pressure-sensitive adhesive, after the absorption, the polymer must have a swelling capacity of at least 30 g/g (i.e. at least 30 parts by weight per part by weight thereof) of physiological saline when it is allowed to freely swell in order to be released from the fixation during the absorption. When the swelling capacity is less than 30 g/g, the swelling pressure is too low to release the polymer from the fixation and the swelling rate of the absorbent polymer fixed with the adhesive is extremely low due to the restraining effect of the adhesive.

Even when the swelling rate of the absorbent polymer is high, the swelling of the polymer is seriously inhibited when the fixing power (adhesive power) of the pressure-sensitive adhesive is higher than the swelling power of the polymer. Thus the pressure-sensitive adhesive must have an adhesive power of 500 to 4000 g in terms of 180° peel adhesion (JIS C 2107) as the representative property. In this case, the properties of the absorbent material must be well-balanced with those of the absorbent polymer as described above. A preferred prerequisite is that the absorbent polymer is in an environment where it can be sufficiently swollen.

The present invention will be further described by referring to the following Examples and Comparative Examples which should not be considered as limiting the present invention.

[Examples and Comparative Examples]

Table 1 shows the results of the following tests referring to the Example products and Comparative products which will be mentioned hereunder.

TABLE

| | | Physical properties of constituting material | | | | Properties of absorbent sheet | | | |
|---|---|---|---|---|---|---|---|---|---|
| | | Klemm water absorption of absorbent material (mm) | absorbent polymer | | adhesive power of pressure-sensitive adhesive (g) | absorption of polymer in absorbent sheet (g/g) | quantity of liquid return | falling of polymer | |
| | | | absorption (g/g) | absorption velocity (ml/0.3 g · 20 min) | | | | quantity of falling (g) | macroscopic evaluation |
| Ex. No. | 1 | 31 | 50 | 10.5 | 3010 | 48 | 0.3 | 0.01 or less | ○ |
| | 2 | 55 | 50 | 10.5 | 2850 | 46 | 0.1 | 0.01 or less | ○ |
| | 3 | 25 | 40 | 8.5 | 3010 | 35 | 0.5 | 0.01 or less | ○ |
| Comp. Ex. No. | 1 | 31 | 50 | 10.5 | water spray only | 45 | 0.4 | 0.25 | X |
| | 2 | 31 | 50 | 10.5 | breakage of base during peeling | 21 | 4.3 | 0.06 | △~X |

(Details of test)

(1) Test on falling off of absorbent polymer:

An absorbent sheet cut to a size of 70×200 mm is weighed and put in a polymer bag having a size of 280×200 mm with a fastener. The bag is shaken by hand 50 times. After the completion of the test, the change in the weight of the absorbent sheet is determined and the water colored with Blue No. 1 (0.3 g/100 ml of water) is added thereto so that the absorbent polymer which falls in the bag can be well observed. The absorbent polymer thus swollen is observed to determine the extent of falling with the naked eye.

○: the absorbent polymer fell off scarcely,
△: the absorbent polymer fell off a little,
X: the absorbent polymer fell off considerably.

The test is repeated 10 times and the quantity of the fallen absorbent polymer is expressed in terms of the average thereof.

(2) Determination of absorption (quantity of liquid absorbed by the absorbent polymer in the absorbent sheet):

The absorbent sheet cut to a size of 70×200 mm is weighed and the weight thereof is referred to as $W_O$. It is then put on a 10-mesh metal gauze and a large excess of physiological saline is poured thereon to saturate the absorbent sheet. After leaving it to stand for 30 min, the physiological saline absorbed by other materials than the absorbent polymer in the absorbent sheet is removed by centrifugation. The absorbent sheet is weighed and the weight thereof is referred to as $W_1$. Then an absorbent sheet having the same structure but free from the absorbent polymer is prepared and subjected to the same procedure as that described above. The initial-weight and the weight after the centrifugation are referred to as $X_0$ and $X_1$, respectively. The quantity of the liquid absorbed in the absorbent polymer in the absorbent sheet is calculated according to the following formula:

[Numerical formula 1]

absorption $(g/g) = [(W_1-W_0)-(X_1-X_0)]/[\text{quantity of dispersed polymer } (g/m^2) \times (\text{area of sample } 0.07 \times 0.20 \ m^2)]$.

(3) Determination of quantity of returned liquid:

10 g of an artificial blood is poured on an absorbent sheet cut to a size of $70 \times 200$ mm and left to stand for 3 min. Then a pile of 10 sheets of filter paper (TYPE 2 of Toyo Roshi Kaisha Ltd.) is put thereon and a pressure of 50 $g/cm^2$ is applied thereto to determine the quantity of the artificial blood returned to the filter paper.

Quantity of returned liquid = (weight of filter paper after compression) - [weight of filter paper before compression (initial stage)]

(4) Determination of absorption (absorbent polymer): 1 g of the absorbent polymer is dispersed in a large excess of physiological saline to thoroughly swell it. Then the absorbent polymer is filtered through an 80-mesh metal gauze and weighed. The absorption is expressed in terms of the weight thus obtained.

Figure 2:
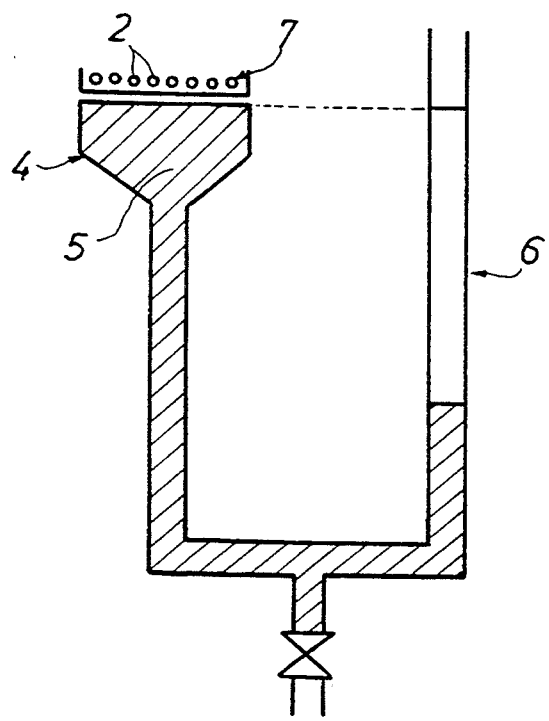
FIG. 2 is a cross section of an apparatus for determining the absorption velocity of the absorbent polymer.

(5) Determination of absorption velocity (absorbent polymer):

The absorbent velocity is determined with the apparatus shown in FIG. 2. The surface of a physiological saline 5 contained in a buret 6 is adjusted to the same level as that of a sample mount 4. 0.3 g of an absorbent polymer 2 is evenly spread on a glass filter 7 having a diameter of 70 mm put on the sample mount 4. The absorption velocity of the absorbent polymer 2 is expressed in terms of the volume of the physiological saline 5 absorbed in the absorbent polymer 2 in 20 min (ml/0.3 g polymer, 20 min).

(Examples of articles)

EXAMPLE 1

20 $g/m^2$ of a hot melt adhesive a [Topco P-618B (trade name of Toyo-Petrolite Co., Ltd.] is spirally applied to an absorbent paper A (33 $g/m^2$ Klemm absorption: 30 mm after 1 min) comprising 100% chemical pulp prepared by the wet paper making method. Further the occupied area of the adhesive-applied part is 45% and the width of the spiral form is approximately 0.05mm to 0.1 mm. Then an absorbent polymer X (sodium acrylate crosslinked polymer, absorption: 50 g/g, absorption velocity: 10.5 ml/0.3 g 20min) is spread thereon in an amount of 45 $g/m^2$ (basis weight). Another sheet of the absorbent paper A is put thereon and compressed into one piece to obtain an absorbent sheet 1 of the present invention.

EXAMPLE 2

40 $g/m^2$ of a hot melt adhesive b (MQ-916, trade name of Kanebo-NSC Ltd.) is sprayed to form dots on an absorbent paper B (25 $g/m^2$ Klemm absorption: 50 mm after 1 min) comprising 30% of chemical pulp and 70% of rayon. Further the occupied area of the adhesive-applied part is 60% and the adhesive is applied in dot pattern of dot having 1 mm to 2 mm in diameter. Then an absorbent polymer X is spread thereon in an amount of 70 $g/m^2$ (basis weight). Another sheet of the absorbent paper B is put thereon and compressed into one piece to obtain an absorbent sheet 2 of the present invention.

EXAMPLE 3

An absorbent sheet 3 of the present invention is prepared in the same manner as that of the Example 1 except that the absorbent paper A is replaced with a nonwoven fabric 9 (basis weight: 35 $g/m^2$ Klemm absorption: 25 mm after 1 min) comprising polyethylene/polyester complex fibers which had been treated to make them hydrophilic, that the absorbent polymer X is replaced with an absorbent polymer Y (sodium acrylate crosslinked polymer, absorption: 40 g/g, absorption velocity: 8.5 ml/0.3 g 20.min) and the basis weight is altered to 20 $g/m^2$ to obtain the absorbent sheet 3 of the present invention.

Comparative Example 1

The same procedure as that of the Example 1 is repeated except that the absorbent polymer X is spread on the absorbent paper A after spraying water thereon without using the hot melt adhesive a and then the absorbent paper A is put thereon and compressed to form a piece to obtain a comparative product 1.

Comparative Example 2

The same procedure as that of the Example 1 is repeated except that the hot melt adhesive is replaced with 20 $g/m^2$ of adhesive A (Movinyl 710 mf. by Hoechst Gosei K.K.) to obtain a comparative product 2.

The absorbent sheets 1 to 3 obtained in the Examples 1 to 3 of the present invention and the comparative products 1 and 2 are subjected to the tests to determine the quantity of fallen absorbent polymer and absorption by the absorbent polymer in each case. The results are given in Table 1.

It is apparent from this Table that the absorbent sheet of the present invention exhibits an excellent effect in the fixation of the absorbent polymer and that the absorbing properties of the absorbent polymer can be exhibited to a full extent.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. An absorbent sheet used for part or all of the absorbent element in an absorbent article comprising
   (1) a liquid permeable layer,
   (2) a liquid-retentive absorbent sheet, and
   (3) a liquid impermeable anti-leakage material wherein said liquid-retentive absorbent sheet is disposed between said liquid permeable layer and said liquid-impermeable anti-leakage material, said absorbent sheet comprising
   (a) a first layer of absorbent material having liquid absorbency, (b) a second layer of absorbent material having liquid absorbency, and (c) an absorbent polymer fixed to said first layer of said absorbent material and said second layer of said absorbent material with a hot melt adhesive in the form of at least one dot, at least one line, or at least one curved line disposed between said first layer of said absorbent material and said second layer of said absorbent material, wherein said absorbent polymer has a liquid absorbency different from that of said absorbent material, and wherein said difference in said liquid absorbency between said absorbent polymer and said absorbent material being sufficient so that liquid, once absorbed in said absorbent material, will smoothly migrate to said absorbent polymer, wherein a size of said dot is 0.1 to 10 mm in diameter, said line or curve line is 0.05 to 5 mm in width and a width of a part to which said adhesive is not applied between said lines is 0.05 to 10 mm, and a part to which the adhesive is not applied exists in a circle of 10 to 30 mm in diameter.

2. An absorbent sheet used for part or all of the absorbent element in an absorbent article comprising (1) a liquid permeable layer, (2) a liquid-retentive absorbent sheet, and (3) a liquid impermeable anti-leakage material wherein said liquid-retentive absorbent sheet is disposed between said liquid permeable layer and said liquid-impermeable anti-leakage material, said absorbent sheet comprising a first layer of absorbent material having liquid absorbency, a second layer of absorbent material having liquid absorbency, and an absorbent polymer fixed to said first layer of said absorbent material and said second layer of said absorbent material with a pressure-sensitive adhesive in the form of at least one dot, at least one line, or at least one curved line, wherein said absorbent polymer has a liquid absorbency different from that of said absorbent material, and wherein said difference in said liquid absorbency between said absorbent polymer and said absorbent material being sufficient so that liquid, once absorbed in said absorbent material, will smoothly migrate to said absorbent polymer, wherein a size of said dot is 0.1 to 10 mm in diameter, said line or curve line is 0.05 to 5 mm in width and a width of a part to which said adhesive is not applied between said lines is 0.05 to 10 mm, and a part to which the adhesive is not applied exists in a circle of 10 to 30 mm in diameter.

3. The absorbent sheet of claim 2 wherein the Klemm absorption height of the absorbent material after one minute is from 20 mm to 150 mm.

4. The absorbent sheet of claim 2 wherein the average capillary size of the absorbent material is 0.5 $\mu$m to 300 $\mu$m.

5. The absorbent sheet of claim 2 wherein the absorbent polymer has an absorbing capacity of 8.0 ml/0.3 g in 20 minutes to 20 ml/0.3 g in 20 minutes.

6. The absorbent sheet of claim 2 wherein the absorbent polymer is present in an amount of 10 g/m$^2$ to 150 g/m$^2$.

7. The absorbent sheet of claim 2 wherein the 180° peel adhesion of the adhesive is 500 g to 4000 g.

8. The absorbent sheet of claim 7 wherein the area occupied by the adhesive is in the range of 10% to 70%.

9. The absorbent sheet of claim 2 wherein the adhesive is applied in an amount of 1 to 50 g/m$^2$.

10. The absorbent sheet of claim 2 wherein the capillary power of the absorbent material is $0.2 \times 10^4$ to $1.5 \times 10^4$ dyn/cm$^2$.

11. A sanitary napkin, comprising the absorbent sheet of claim 2.

12. A paper diaper, comprising the absorbent sheet of claim 2.

13. A surgical pad, comprising the absorbent sheet of claim 2.

14. A breast milk sheet, comprising the absorbent sheet of claim 2.

* * * * *